US008608788B2

(12) United States Patent
Starr et al.

(10) Patent No.: US 8,608,788 B2
(45) Date of Patent: Dec. 17, 2013

(54) UNDERBODY CONVECTIVE BLANKET AND METHOD FOR MANUFACTURING THEREOF (75) Inventors: Rachel Starr, Randolph, MA (US);
Joseph Pierre, Brockton, MA (US);
Daniel Reardon, Abington, MA (US);
Alan Stec, East Bridgewater, MA (US)

(73) Assignee: Smiths Medical ASD, Inc., Rockland, MD (US)

( * ) Notice: Subject to any disclaimer, the term of this patent is extended or adjusted under 35 U.S.C. 154(b) by 1280 days.

(21) Appl. No.: 12/078,400

(22) Filed: Mar. 31, 2008

(65) Prior Publication Data
US 2009/0248120 A1    Oct. 1, 2009

(51) Int. Cl.
A61F 7/00    (2006.01)

(52) U.S. Cl.
USPC ........................................ 607/108

(58) Field of Classification Search
USPC ................... 607/108–112, 114
See application file for complete search history.

(56) References Cited

U.S. PATENT DOCUMENTS

| | | |
|---|---|---|
| 5,125,238 A | 6/1992 | Ragan et al. |
| 5,675,848 A | 10/1997 | Kappel |
| 5,749,109 A | 5/1998 | Kappel |
| 6,102,936 A | 8/2000 | Augustine et al. |
| 6,156,058 A | 12/2000 | Kappel et al. |
| 6,277,144 B1* | 8/2001 | Tomic-Edgar et al. ....... 607/108 |
| 6,827,729 B2 | 12/2004 | Gammons et al. |
| 6,942,687 B1 | 9/2005 | Heaton et al. |
| 2003/0023290 A1 | 1/2003 | Gammons et al. |
| 2006/0142825 A1 | 6/2006 | Dunlop |
| 2006/0282140 A1* | 12/2006 | Schock et al. ............... 607/108 |
| 2007/0244532 A1 | 10/2007 | Pierre et al. |

FOREIGN PATENT DOCUMENTS

| | | |
|---|---|---|
| EP | 1126802 | 8/2001 |
| WO | 00/04853 | 2/2000 |
| WO | 00/19946 | 4/2000 |
| WO | 03/011110 | 2/2003 |
| WO | 2004/052250 | 6/2004 |
| WO | 2007/120677 | 10/2007 |

* cited by examiner

Primary Examiner — Nicholas Lucchesi
Assistant Examiner — Melissa A Snyder
(74) Attorney, Agent, or Firm — Louis Woo (57) ABSTRACT A convective underbody blanket has a head portion and a body portion. Provided at the head portion is a non-inflatable head area surrounded by a channel that has arranged thereat at least one row of air apertures that are oriented toward the non-inflatable head area when the channel is inflated. At the body portion there is provided a non-inflatable body area. Along each longitudinal side of the body area there is at least one longitudinal channel. Each of the longitudinal channels is in fluid communication with the channel that surrounds the non-inflatable head area. The longitudinal channels that sandwich the non-inflatable body area extend substantially along the length of the non-inflatable body area and are in fluid communication with each other by way of a cross channel formed at the foot end of the blanket. The configuration of the blanket allows air input to the blanket to be circulated through the various channels, so that the heated air output from the different rows of apertures formed at the various channels has substantially the same temperature. The different rows of apertures may be provided at different areas along the blanket.

20 Claims, 6 Drawing Sheets

UNDERBODY CONVECTIVE BLANKET AND METHOD FOR MANUFACTURING THEREOF

FIELD OF THE INVENTION

The present invention relates to convective warming blankets and more particularly to an underbody blanket for convectively warming both the head and the body of the patient.

BACKGROUND OF THE INVENTION

There are underbody convective blankets in the market. One of those blankets is described in U.S. Pat. No. 6,511,501. However, the '501 blanket is not meant to provide warmth to the head of the patient via convection. There are moreover a number of other blankets represented for example by U.S. Pat. Nos. 5,360,439, 5,384,924, 5,514,169, 5,632,769 and 5,839,133 that specifically have a recess at the head end of the blanket whereby the head of the patient lies.

There are some convective blankets that could warm the head of the patient. However, most of those blankets are for covering the body of the patient. An example of such blankets is disclosed in U.S. Pat. No. 5,928,274 in which the head portion of the blanket has a recess so that only the head of the patient is not covered by the blanket.

Also with respect to the prior art convective blankets, the apertures or holes whereby the warm air is output from the blanket usually are pre-punched before the two layers of the blanket are bonded so that the apertures are substantially evenly distributed across the sheet of the blanket that outputs the warm air. That being the case, the heated air output from the blanket is directed to the patient without much focus. Furthermore, for the prior art underbody blankets, at least with respect to those that are full body convective blankets, the channels that extend longitudinally along the blanket usually would extend all the way to the foot end of the blanket, so that the air input to the blanket flows substantially in only one direction. This means that by the time that the heated air gets to the foot end of the blanket, the warmth of the air has substantially diminished. Accordingly, there is a temperature gradient difference between the heated air output proximally to the air inlet port and the heated air output distally from the air inlet port.

A need therefore exists for a new type of underbody blanket that warms the head, as well as the body of the patient, with the warm air circulating about the blanket to maintain an even temperature throughout, and when output from the blanket, is focused to the patient.

SUMMARY OF THE PRESENT INVENTION

The convective blanket of the instant invention is an underbody blanket that is designed to support the entire body of the patient, including the head of the patient. As such, the blanket is configured to have a head portion and a body portion, with the head portion extending from the head end of the blanket to the beginning of the body portion, which extends to the foot end of the blanket.

To receive the head of the patient, there is formed at the head portion a non-inflatable head area. This head area is encircled by a channel or through passage where fluid such as air passes. There are a number of rows of air holes or apertures that are arranged in a configuration that follows the outline of the non-inflatable head area. The rows of apertures may be substantially in parallel and are arranged such that if the channel were inflated, the apertures would be oriented towards the non-inflatable head area to substantially point towards the head of the patient. Accordingly, air output from the apertures is directed to the head of the patient. When the channel is inflated and heated air circulates through the channel at the head portion, the patient's head, which is received in the non-inflatable head area, is bathed by the warm air output from the apertures.

Extending from the head portion is the body portion. There is formed in the body portion a non-inflatable body area onto which the body of the patient, or at least a portion of the body of the patient, is received. There are extending along each longitudinal side of the non-inflatable body area a number of channels, in this embodiment two adjacent channels separated by a longitudinal seal. There is formed at each of the channels at least one row of air apertures arranged along the channels such that when the channels are inflated, these apertures would point to or be oriented toward the non-inflatable body area. Air output from the apertures accordingly would be directed to the patient's body lying on the non-inflatable body area. By providing multiple channels along each longitudinal sides of the non-inflatable body area, the height or vertical profile of the blanket when fully inflated is reduced. The longitudinal channels that run along the sides of the non-inflatable body area extend substantially towards the distal end of the non-inflatable body area.

A cross channel is formed between the distal end of the non-inflatable body area and the foot end of the blanket to establish a fluid path or through passage between the sets of adjacent channels that extend longitudinally along the non-inflatable body area.

By thus connecting the longitudinal channels that sandwich the non-inflatable body area with both the cross section at the foot end of the blanket and the channel that circumscribes the non-inflatable head area of the blanket, continuous through passages are established throughout the convective blanket so that air input to the blanket via any one of the open channels is circulated throughout the blanket with the heated air being output from the various rows of apertures directly to the desired areas of the patient lying on top of the blanket.

To input air to the blanket, at least one air inlet is provided. However, for the exemplar blanket embodiment, three air inlets may be provided. These air inlets may be configured the same as that disclosed in U.S. application Ser. No. 11/401,957 entitled "Hose Retainer for Thermal Blanket", assigned to the same assignee as the instant invention. The disclosure of the '957 application is incorporated by reference herein. By providing two of the air inlets at the respective shoulders of the blanket and an air inlet at the foot of the blanket, air may be input to the blanket at any one of those different locations on the blanket.

To eliminate bodily fluid from the patient that may collect at the non-inflatable body area of the blanket, at least one optional fluid absorption pad may be provided at the patient body area.

There are provided at each longitudinal side of the blanket a flap that allows the blanket to be adhered or attached to the bed or operation table onto which the blanket is placed.

With the inventive underbody blanket, the entire body of the patient lying on the blanket is accessible.

So that a surgeon operating on the patient is not heated by the warm air, another embodiment of the blanket of the instant invention eliminates a number of air apertures along the longitudinal channels that sandwich the non-inflatable body area of the blanket. In this embodiment, the respective rows of apertures that extend along the longitudinal channels adjacent to the non-inflatable body area are partitioned into at least two sets of apertures that are separated by a non-apertured section. The non-apertured section is located along the blanket at an area where the surgeon usually positions when he or she operates on the patient lying on top of the inventive blanket.

A further embodiment of the blanket of the instant invention focuses on concentrating the apertures to particular parts of the blanket so that only corresponding portions of the body of the patient is bathed by the air output from the blanket. A first variant of this embodiment is the provision of respective rows of apertures along the longitudinal channels that sandwich the non-inflatable body area only at the upper portion of the blanket so that only the upper body or chest area of the patient is bathed by the output air. Another variant of the embodiment has the apertures provided only at the lower portion of the blanket along the longitudinal channels that sandwich the non-inflatable body area so that only the lower body and/or foot portion of the patient is bathed by air output from the blanket. All other features of the invention remain the same for this further embodiment.

To manufacture the inventive blanket, two sheets of flexible air impermeable materials are sealed or bonded together at selective locations to form the various channels and non-inflatable head and body areas. Before bonding, the sheet to be in contact with the patient is selectively punched with pre-configured rows of apertures, so that once bonded to the other sheet, the apertures that are at the various channels would be arranged such that when air is input to the blanket and the channels are inflated, the apertures would point towards the non-inflatable areas for directing the output heated air thereat.

The present invention is therefore an underbody convective blanket that comprises a first air impermeable flexible sheet having a plurality of apertures selectively bonded to a second air impermeable flexible sheet at different locations to form an inflatable structure having a head end and a foot end. The structure includes a head portion at the head end and a body portion that extends from head portion to the foot end, with the first sheet of the structure adapted to support the patient lying thereon. The head portion has a non-inflatable head area whereupon the head of the patient lies and the body portion has a non-inflatable body area whereupon at least one portion of the body of the patient lies. There is at least one channel formed in the structure for surrounding the non-inflatable head area and two other channels each in fluid communication with a corresponding opening of the one channel. Each of the other channels extends substantially along a corresponding longitudinal side of the non-inflatable body area. A cross channel is formed at the foot end of the structure to establish a fluid communication path between the two other channels. There is an inlet that enables air to be input to the structure and be circulated through the channels, and output from the apertures toward the patient lying on the structure.

Another aspect of the instant invention relates to a convective underbody blanket having a head end and a foot end that comprises: a head portion extending from the head end having a non-inflatable head area for receiving the head of a patient, a body portion extending from the head portion having a non-inflatable body area for receiving the body (including a part of the body) of the patient, at least one inflatable channel at the head portion to surround the non-inflatable head area, at least two inflatable other channels at the body portion each in fluid communication with a corresponding opening of the one channel and each extending substantially along a corresponding longitudinal side of the non-inflatable body area, an inflatable cross channel formed at the foot end of the blanket to establish a fluid communication path between the other channels, a plurality of apertures formed at the one and other channels, and at least one inlet provided to the blanket to enable air to be input into and circulate through the channels.

The instant invention also relates to a method of manufacturing an underbody convective blanket that includes the steps of: punching a plurality of apertures on a first air impermeable flexible sheet, selectively bonding the first air impermeable flexible sheet to a second air impermeable flexible sheet at different locations to form an inflatable structure that has a head end and a foot end, a head portion at the head end that has a non-inflatable head area to receive the head of the patient and a body portion extending from the head portion to the foot end having a non-inflatable body area to receive the body of the patient. The bonding step further includes the step of forming at least one channel in the structure to surround the non-inflatable head area, forming at least two other channels each in fluid communication with a corresponding opening of the one channel, extending each of the other channels substantially along a corresponding longitudinal side of the non-inflatable body area and forming a cross channel at the foot end of the structure to establish a fluid communication path between the channels. The method further includes the step of forming at least one inlet to the structure to enable air to be input into and to circulate through the channels, and to output from the apertures.

BRIEF DESCRIPTION OF THE FIGURES

The present invention will become apparent and the invention itself with be best understood with reference to the following description of the present invention taken in conjunction with the accompanying drawings wherein.

DETAILED DESCRIPTION OF THE INVENTION

Figure 1:
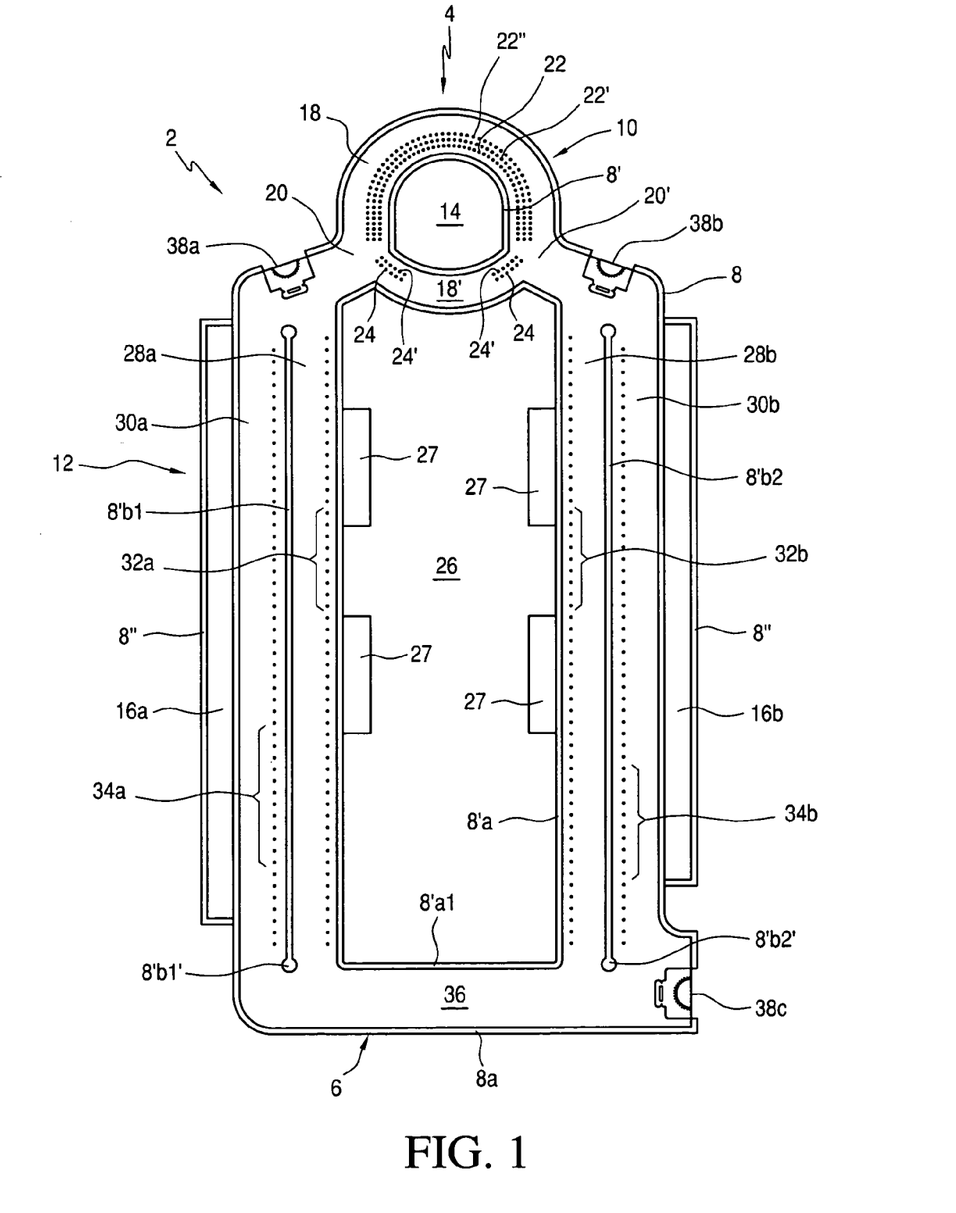
FIG. 1 is a top view of the blanket of the instant invention.

With reference to FIG. 1, a convective underbody blanket 2 is shown to have a head end 4 and a foot end 6. The blanket is made of two sheets of flexible air impermeable material that are bonded together. The bonding of the first or top flexible air impermeable sheet to the second or bottom flexible air impermeable sheet is done by seals such as 8, 8' and 8" shown. Seal 8 designates the outer seal that forms the outer periphery of blanket 2. Seal 8" designates the seals that, together with seal 8, form the outer flaps 16a and 16b of the blanket. Seal 8' designates the internal seals of the blanket. Thus bonded, the flexible air impermeable sheets form blanket 2 that has a head portion 10 and a body portion 12.

In head portion 10 there is a non-inflatable head sub-portion, or area 14. Non-inflated head area 14 is surrounded by a channel 18 that has two openings 20 and 20'. It should be appreciated that even though only one channel 18 (which includes to be discussed lower channel 18') is shown to surround head area 14, there may in practice be a multiple number of channels 18 formed at the head portion 10 to circumscribe head area 14.

As shown, there are three rows of air apertures 22, 22' and 22" that substantially surround the head portion of the non-inflatable head area 14. There are in addition two rows of apertures 24 and 24' that are located at the lower portion of the non-inflatable head area 14, which happens to be the lower portion of channel 18, designated 18'. For the blanket embodiment shown in FIG. 1, channel 18 therefore substantially circumscribes the non-inflatable head area 14, except for openings 20 and 20'. The rows of apertures 22 (including 22' and 22") are arranged such that when channel 18 is inflated, due to the flexible nature of the upper sheet, apertures 22 would substantially shift or orient upwardly at an angle relative to the horizontal plane of the blanket as channel 18 rises. The apertures end up pointing towards the non-inflatable area 14 at an angle, after channel 18 has been substantially fully inflated. The apertures would direct the air circulating in channel 18 out towards the non-inflatable area 14, and therefore focus the warm air to the head of the patient lying thereon. Apertures 24 at the lower head portion provide heat to the neck and head of the patient.

The body portion 12 of blanket 2 extends from head portion 10 to the foot end 6. As shown, the body portion 12 has a non-inflatable body area 26 that extends substantially from the head portion, or channel 18', to substantially the foot end 6. For the FIG. 1 embodiment, there may be provided in either or both of the non-inflatable head area 14 and non-inflatable body area 26 at least one optional fluid absorbent pad for absorbing fluids, which may result from sweat and/or other fluids from the patient, or some other source, collected on the blanket. As shown in the exemplar blanket of FIG. 1, there are four fluid absorbent pads 27 provided at body area 26. These pads may be attached to the blanket by tape, Velcro or other types of adhesive. Although not shown, at least one fluid absorbent pad may likewise be attached to head area 14.

Surrounding body area 26, at each longitudinal sides thereof are respective pairs of longitudinal channels 28a, 28b and 30a, 30b. Channels 28a and 28b are formed adjacent to body area 26 and are isolated therefrom by seal 8'a. Channels 30a and 30b are further removed from body area 26 and are separated from channels 28a and 28b, respectively, by seals 8'$b_1$ and 8'$b_2$. In place of two channels 28 and 30, the inventive blanket may utilize only one or more than two channels along each longitudinal side of body area 26. Empirical studies show two pairs of adjacent channels to be desirable in that the warming of the patient lying on the blanket continues to be good while the vertical profile of the inflated blanket is lowered to an acceptable height. For example, instead of a six inch rise for a single channel at each side of the patient body area 26, with two adjacent channels, the rise in the vertical profile of the blanket would only be approximately 3 inches when the blanket is fully inflated.

Provided along each of the longitudinal channels 28 and 30 are apertures, in most instances evenly spaced, that extend in a row along the length of each of the channels. The apertures are biased towards the non-inflatable body area 26. These rows of apertures are designated 32a and 32b (for channels 28a and 28b, respectively) and 34a and 34b (for channels 30a and 30b, respectively). Each of the rows of apertures 32a, 32b 34a and 34b is arranged along its corresponding channel such that when the channels are inflated, the respective rows of apertures will orient at an angle, relative to the horizontal plane of the blanket, towards the non-inflatable body area 26. As a consequence, air output from the apertures is directed to the body area 26, and focused to particular portions of the body of the patient lying thereon.

As was discussed above, apertures 22, 32 and 34 are pre-punched in the top air impermeable sheet so that when the top sheet is bonded to the bottom sheet, the rows of apertures 22, 32 and 34 would lie substantially adjacent their respective seal lines 8', 8'$a_1$ and 8'$b_1$, respectively. This ensures that when the blanket is inflated, as the respective channels containing the apertures are inflated, the respective rows of apertures would be orientated towards the head area 14 and the body area 26. Of course, if there are additional channels, additional rows of apertures similarly arranged would be added. Also, as was noted before, instead of dual channels 28 and 30, if the blanket profile height is of no importance, there may only be one longitudinal channel provided along either side of body area 26.

As shown in FIG. 1, channels 28a and 30a each are in fluid communication with channel 18, 18' by way of opening 20, while channels 28b and 30b each are in fluid communication with channel 18, 18' via opening 20'. Channels 28 and 30 from each side of body area 26 extend substantially from the head portion to the lower portion of the blanket proximate to seal 8'$a_1$, by way of their respective seal ends 8'$b_1$, and 8'$b_2$.

A cross channel 36 is formed at foot end 6 between seal 8'$a_1$ and the lowermost seal 8a. Thus formed, the cross channel 36 establishes a through passage or fluid communications path for channels 28a, 30a and channels 28b, 30b. The non-inflatable body area therefore is circumscribed by through passages in the form of channels 28, 30 and 36, as well as channel 18'; while the non-inflatable head area 14 is circumscribed by channels 18 and 18'. Given that channel 18 and channels 28, 30 are interconnected, when the blanket is inflated by pressurized heated air and the blanket inflation is maintained, the heated air is circulated throughout the blanket. Thus, the temperature of the heated air remains substantially the same throughout the blanket. Accordingly, temperature gradient differences among the various areas of the blanket that exist in prior art convective blankets are substantially eliminated, as the heated air output from the various rows of apertures to bathe the patient for the inventive blanket has substantially the same temperature, for example within 1 to 5° centigrade difference.

To enable air to be input to blanket 2, there is at least one air inlet provided. For the inventive blanket of FIG. 1, three inlet ports 38a, 38b and 38c are provided. Inlet ports 38a and 38b each are provided at a corresponding shoulder section of blanket 2, while inlet port 38c is provided at the foot end of blanket 2. Each of those air inlets may be made of a foldable hose retainer port described in greater detail in the above incorporated by reference application Ser. No. 11/401,957. By having a multiple number of air inlet ports, the anesthesiologist is able to arrange his equipment at multiple locations relative to blanket 2.

In operation, the selected air inlet port may be folded into a box shape to accept an air hose (not shown) so that pressurized heated air may be force fed into the blanket by a hot air blower, such as for example the EQUATOR convective air warmer sold by the assignee of the instant invention.

Figure 2:
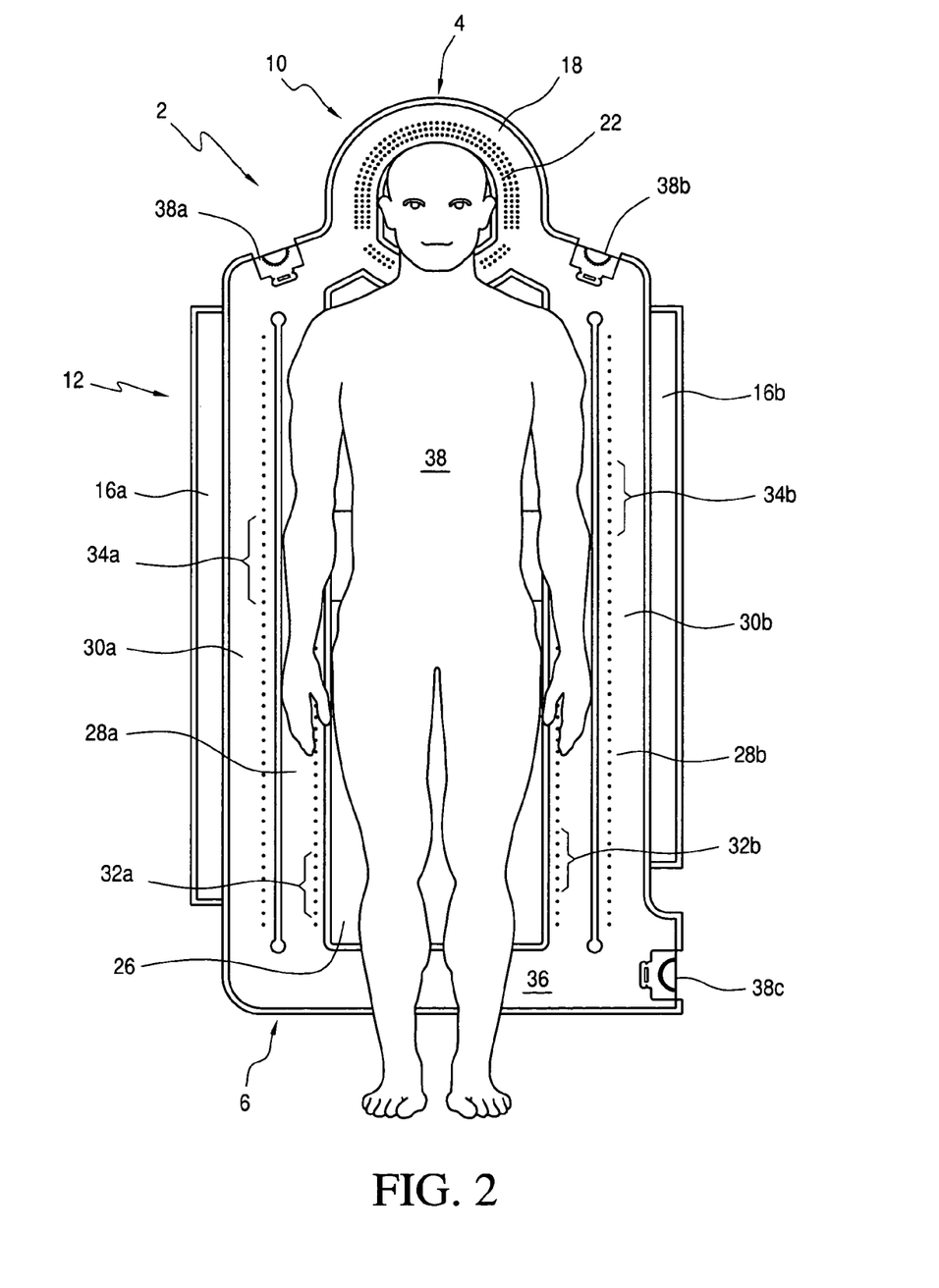
FIG. 2 is a top view of the blanket of the instant invention having a patient lying thereon.

FIG. 2 shows a patient 38 resting on blanket 2. As shown, the head of the patient is resting on the non-inflatable head area 14 (shown more clearly in FIG. 1) while the body of the patient is resting on the non-inflatable body area 26. Given the positioning of the patient on blanket 2, it can readily be seen that the heated air output from the different rows of apertures 22 is directed to the head of a patient while the air output from the rows of apertures 32a, 32b and 34a, 34b is directed to warm the body of the patient.

Presuppose the pressurized and presumably heated air is input to the blanket via inlet port 38b. The input air therefore would circulate through channels 18, 18', 28 and 30, and 36 around the blanket. Once the blanket is fully inflated and the input air maintains the channels at equilibrium inflation, the air output from the various apertures would tend to have substantially the same temperature, or substantially the same temperature gradient (for example from ambient to 44° C. at the air inlet location to ±5° C. variance across the blanket), to warm the patient. By providing multiple rows of apertures at head portion 10, the head of the patient is exposed to more heated air. To secure the blanket to the bed or the operating table, flaps 16a and 16b at the sides of the blanket may be taped or tied to the bed or the operating table.

Figure 3:
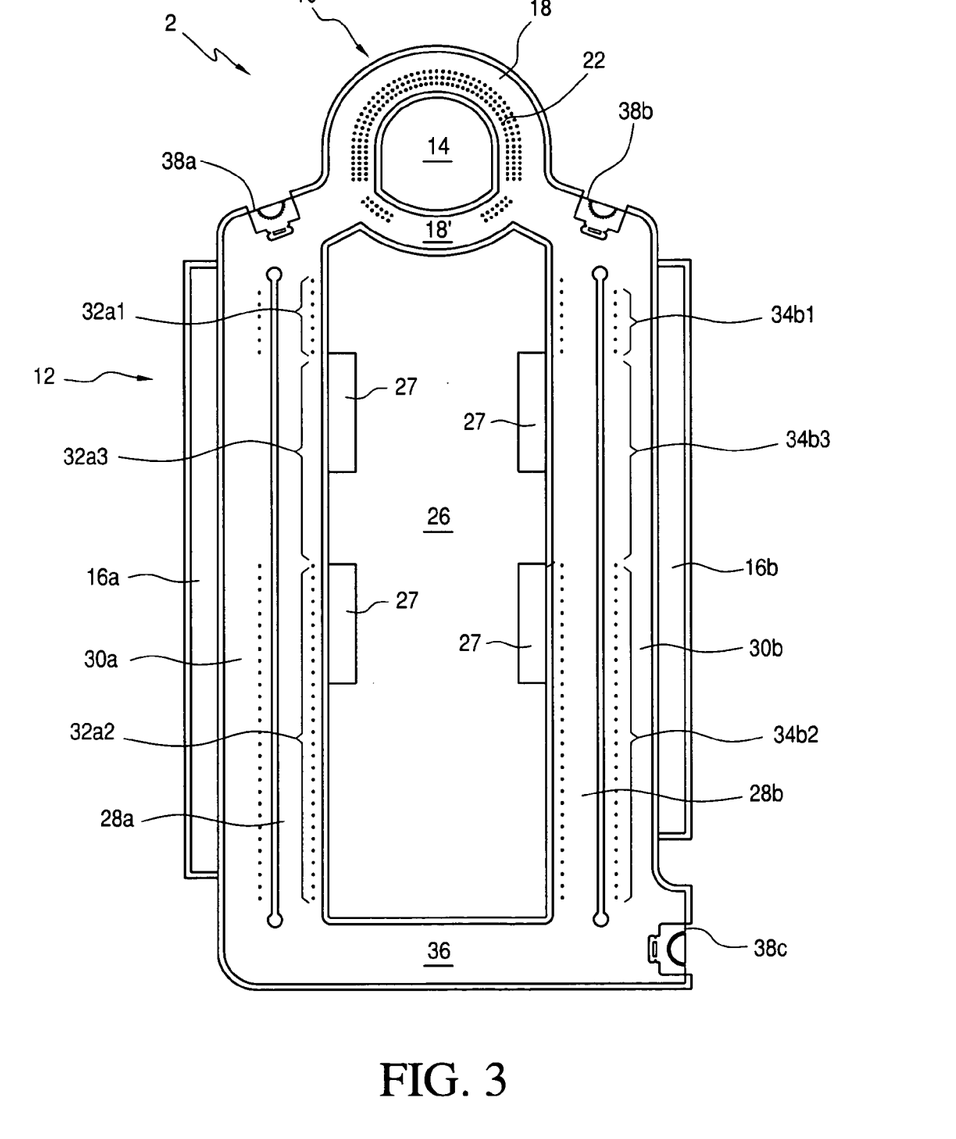
FIG. 3 is another embodiment of the blanket of the instant invention.

FIG. 3 shows an alternative embodiment of the instant invention where the respective rows of apertures at the longitudinal channels 28 and 30 are discontinuous. Putting it differently, each of those rows of apertures is made up of two sets or two sections of apertures separated by a non-apertured section. Point of illustration. At channel 28a, what used to be a row of apertures 32a is now divided into apertured sections $32a_1$ and $32a_2$, separate by a non-apertured section $32a_3$. The same apertured sections separated by a non-apertured section layout is repeated for channels 32a, 28b and 30b of blanket 2. For ease of illustration, only the sections of channels 28a and 30b are numbered in the FIG. 3 embodiment blanket.

With no apertures provided at the non-apertured section such as $32a_3$ and $34b_3$, no air is output from those portions of the blanket. This is advantageous in the instance where the surgeon operating on the patient does not want to be heated by the warm air output from the convective blanket. By thus removing the air apertures from those sections of the blanket as shown, which happens to be where the surgeon usually is positioned relative to the patient when he or she operates on the patient, the surgeon is not directly heated by the air output from the blanket. Also, there may be instances where the area of the patient that is being operated on should not be directly subjected to heated air. With the blanket embodiment of FIG. 3, the being operated area of the patient no longer is directly exposed to heated air. Instead, that area of the patient is heated by air conduction, whereas the remainder of the patient continues to be directly warmed by heated air output from the apertures in a convective manner.

Figure 4:
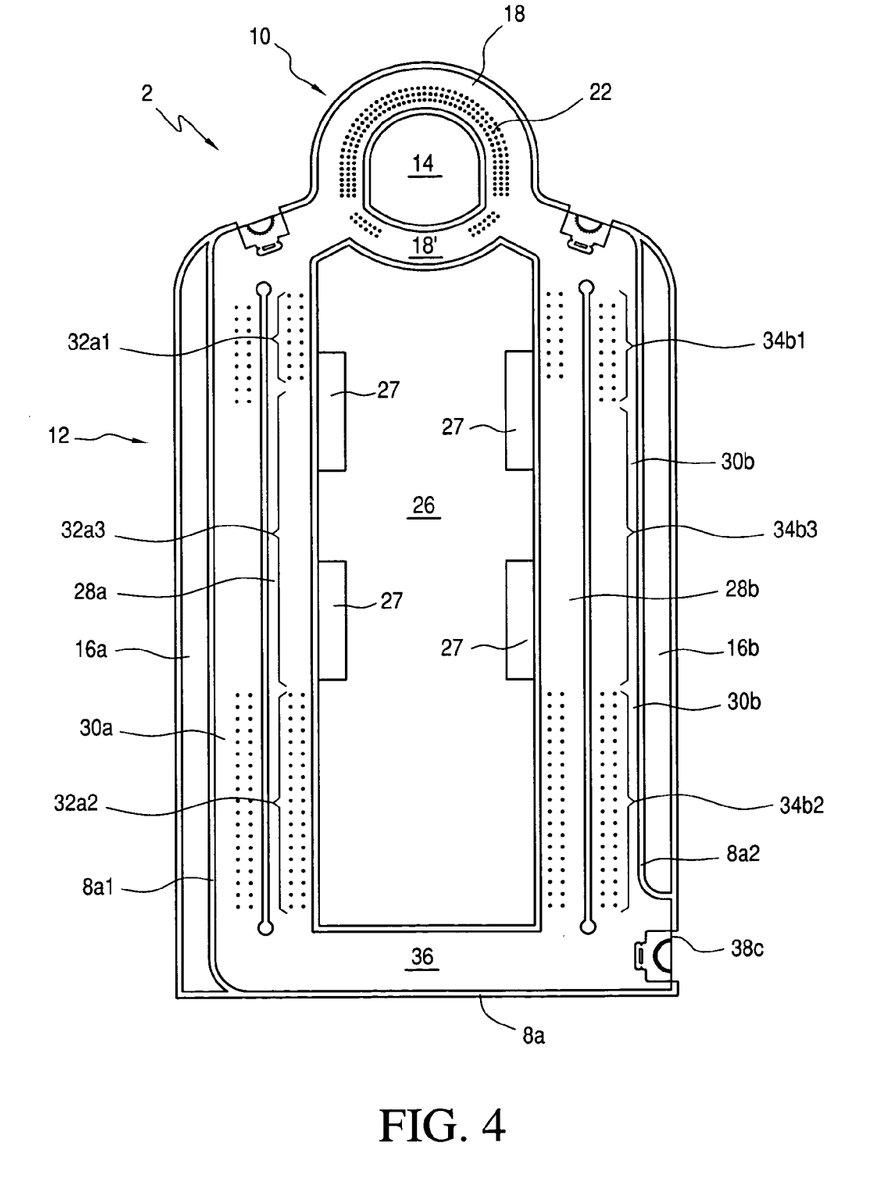
FIG. 4 shows a variant of the FIG. 3 embodiment in which multiple sets of apertures are provided along the selected sections of each of the longitudinal channels.

FIG. 4 is an illustration of a blanket that is a variant of the embodiment of the blanket shown in FIG. 3. Elements that correspond to those in the FIG. 3 embodiment are labeled the same. In particular, instead of respective discontinuous single rows of apertures along each of the longitudinal channels 28a, 28b and 30a, 30b, there are shown two discontinuous parallel rows of apertures along each of the channels. To illustrate, for channel 28a, a non-apertured section 32a3 is sandwiched by a set of double rows of apertures at section 32a1 and a set of double rows of apertures at section 32a2. The same is true for all of the other channels 30a, 28b and 30b shown. Similar to the previously discussed embodiments, the apertures of each channel of the blanket are configured such that when the blanket is inflated, the apertures are oriented toward the center of the blanket so that air output therefrom is directed to the patient lying on the blanket, presumably on the uninflated body area 26 thereof. Although only two rows of apertures are shown at each of the apertured sections, it should be appreciated that more than two rows of apertures may also be used. So, too, in place of two parallel rows, the apertures may be configured to be out of alignment with each other at each of the apertured sections, so long as the non-aligned apertures continue to face toward the non-inflated body area 26 when the blanket is inflated, such that air output from the apertures continues to be directed to the patient.

Another difference between the blanket shown in FIG. 4 and those shown in the earlier figures is the respective lengths of the side flaps 16a and 16b. For the FIG. 4 blanket, flap 16a is longitudinally contiguous along a corresponding side of the outermost longitudinal channel 30a (i.e., separated by seal 8a1), while flap 16b is longitudinally contiguous along the side of the outermost longitudinal channel 30b defined by seal 8a2, up to air inlet 38c.

Figure 5:
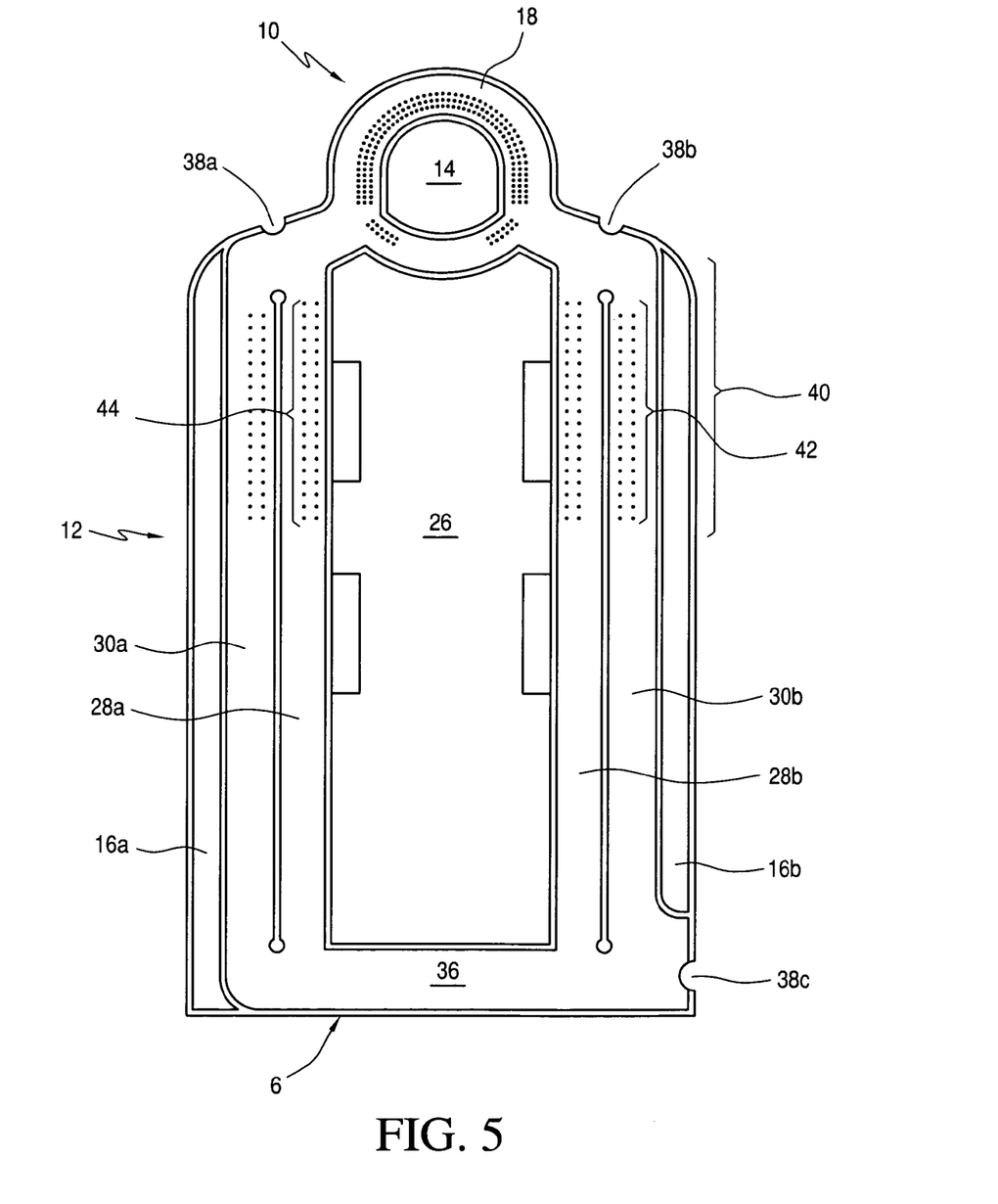
FIG. 5 shows another embodiment of the inventive blanket where the apertures for outputting air to the patient are provided at the upper portion of the blanket.

Another embodiment of the instant invention is shown in FIG. 5. All elements that are the same as in the previous embodiments are designated the same in this embodiment. As shown, the inventive blanket of the FIG. 5 embodiment is configured substantially the same as in the earlier embodiments except for the placement of the apertures or air outlets along the blanket. For this embodiment, air outlet apertures are provided at the upper body portion 40 of the blanket so that air circulating within the blanket is output only to the upper body of the patient lying on the blanket. The apertures are configured and punched as described in the earlier embodiments of the instant invention so that when the blanket is substantially fully inflated, the orientation of the apertures, for example the two rows of the apertures designated 42 at channel 30b is directed to the non-inflatable area 26 so that the air output from the apertures is substantially directed to the upper body of the patient. This is useful in those situations where only the upper body of the patient is to be warmed. As shown in FIG. 5, only the rows of apertures in channels 30b and 28a are labeled, i.e., 42 for channel 30b and 44 for channel 28a. The other apertures shown in FIG. 5 have not been labeled for ease of illustration. Although two rows of apertures are shown at each of the longitudinal channels that sandwich non-inflated body area 26, it should be appreciated that only one row or more than two rows of apertures may be formed at each of the longitudinal channels at the upper body portion 40 of the blanket for bathing the upper body of the patient with the air output from those apertures.

Figure 6:
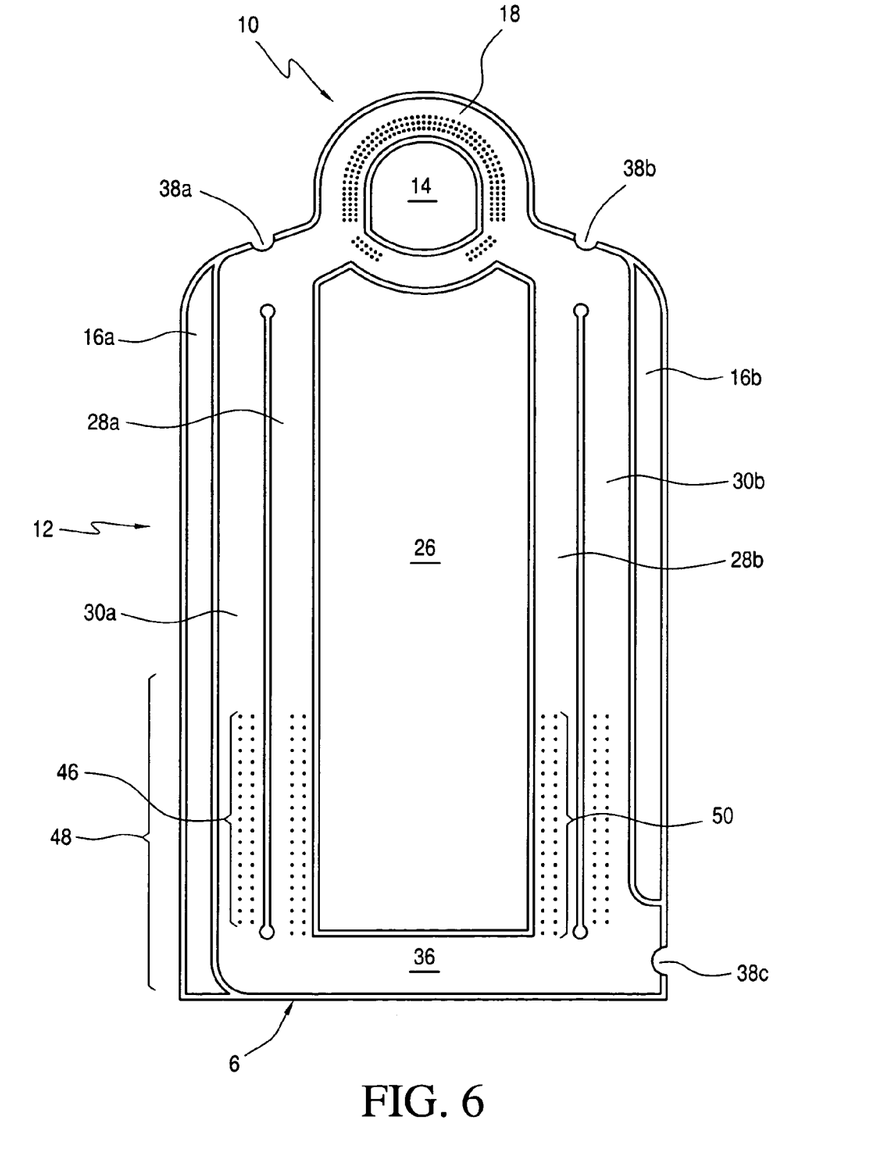
FIG. 6 is another variant of the FIG. 5 blanket where the apertures are provided at the lower body portion of the blanket.

A variant of the FIG. 5 embodiment is shown in FIG. 6. There, instead of being provided at the upper body portion of the blanket, the apertures are provided at the lower body portion 46 of the blanket. Same as before, for ease of illustration, only the apertures 48 along channel 30a and apertures 50 along channel 28b are labeled. As before, instead of the dual parallel rows of apertures provided along the longitudinal channels, only one row or additional rows of apertures may be provided at each of the longitudinal channels for outputting air from the blanket to warm the lower body portion of the patient lying on the blanket. The configuration of the apertures 48 and 50 for the FIG. 6 embodiment is similar to those of the earlier embodiments so that, when the blanket is substantially fully inflated, the apertures would orient toward the non-inflatable body 26 and air output from those apertures is directed substantially only to the lower body portion of the patient.

The present invention is subject to many variations, modifications and changes in details. For example, instead of dual longitudinal channels, there may only be one channel along each side of the non-inflatable body area. Conversely, there may be more than two channels extending longitudinally along each side of the non-inflatable body area. Further, even though only one row of apertures is shown along each of the longitudinal channels, there may in practice be multiple rows of apertures, either continuous evenly spaced rows of apertures or sections of evenly spaced apertures separated by a non-apertured section, biased in the same manner towards the patient body area per shown in the Figures. Thus, it is intended that all matter described throughout this specification and shown in the accompanying drawings be interpreted as illustrative only and not in a limiting sense. Accordingly, it is intended that the instant invention be limited only by the spirit and scope of the hereto appended claims.

The invention claimed is:

1. An underbody convective blanket comprising: a first air impermeable flexible sheet having a plurality of apertures selectively bonded to a second air impermeable flexible sheet at different locations to form an inflatable structure having a head end and a foot end, said structure including a head portion at the head end and a body portion extending from said head portion to the foot end, said first sheet of said structure adapted to support a patient lying thereon; said head portion having a non-inflatable head area enclosed by a non-ending seal whereupon the head of the patient lies and said body portion having a non-inflatable body area enclosed by a non-ending seal whereupon at least one portion of the body of the patient lies; at least one channel formed in said structure for surrounding said non-inflatable head area; said body portion of said structure including at least two other channels each in fluid communication with a corresponding opening of said one channel, each of said other channels extending substantially along a corresponding longitudinal side of said non-inflatable body area; a cross channel formed at the foot end of said structure for establishing a fluid communication path between said other channels; and at least one inlet enabling air to be input to said structure; wherein air input to said structure is circulated through the channels and output from the apertures towards the patient lying on said structure.

2. Blanket of claim 1, wherein respective sets of multiple apertures at said first sheet are formed longitudinally along a corresponding one of said other channels that longitudinally sandwich said non-inflatable body area, each of said sets of multiple apertures being arranged along its corresponding other channel such that when said other channel is inflated, the apertures are oriented towards said non-inflatable body area to thereby direct air output from the apertures towards said non-inflatable body area.

3. Blanket of claim 1, wherein there is at least a pair of first and second other channels formed longitudinally along each side of said non-inflatable body area, said first and second other channels being separated by a longitudinal seal, at least one row of apertures at said first sheet are formed and arranged at each of said first and second channels such that the apertures are oriented towards said non-inflatable body area to direct air output from the apertures towards said non-inflatable body area when said first and second channels are inflated.

4. Blanket of claim 1, wherein respective sets of multiple apertures at said first sheet are formed as at least two in alignment sections of apertures separated by a non-apertured section longitudinally along a corresponding one of said other channels, said sets of apertures along each of said other channels being arranged such that when said other channels are inflated, the apertures are oriented towards said non-inflatable body area to direct air output from the apertures towards said non-inflatable body area, no air being output from said non-apertured section of each of said other channels.

5. Blanket of claim 1, wherein there is at least a pair of first and second other channels formed longitudinally along each side of said non-inflatable body area, said first and second other channels each having two in alignment sections of apertures separated by a non-apertured section, the apertures being oriented towards said non-inflatable body area when said first and second channels are inflated to direct air output from the apertures in a direction towards said non-inflatable body area, no air being output from said non-apertured section of said first and second channels.

6. Blanket of claim 1, further comprising at least one row of apertures formed at said one channel surrounding said non-inflatable head area at at least the head end of said structure, said one row of apertures being arranged at said one channel such that the apertures are oriented towards said non-inflatable head area when said one channel is inflated.

7. Blanket of claim 1, further comprising at least one fluid absorption pad positioned at at least one of said non-inflatable areas to absorb fluid collected thereat.

8. Blanket of claim 1, wherein there are two inlets each provided at a corresponding shoulder of said structure and a third inlet provided at the foot end of said structure, each of the inlets adapted to be selectively opened to enable air to be input to said structure.

9. A convective underbody blanket having a head end and a foot end, comprising:
a head portion extending from the head end having a non-inflatable head area enclosed by a non-ending seal for receiving the head of a patient;
a body portion extending from said head portion having a non-inflatable body area enclosed by a non-ending seal for receiving the body of the patient;
at least one inflatable channel at said head portion surrounding said non-inflatable head area;
at least two inflatable other channels at said body portion each in fluid communication with a corresponding opening of said one channel, each of said other channels extending substantially along a corresponding longitudinal side of said non-inflatable body area;
an inflatable cross channel formed at the foot end for establishing a fluid communication path between said other channels;
a plurality of apertures formed at said one and other channels; and
at least one inlet provided to said blanket to enable air to be input into and circulate through the channels, the air outputting from said plurality of apertures.

10. Blanket of claim 9, wherein said plurality of apertures formed at said one channel comprise at least one row of apertures formed along said one channel and arranged thereon so as to be oriented towards the non-inflatable head area when said one channel is inflated; and
wherein said plurality of apertures formed at said other channels comprise at least two other rows of apertures each formed along a corresponding one of said other channels and arranged to be oriented towards said non-inflatable body area when said other channels are inflated.

11. Blanket of claim 9, wherein there are first and second other channels formed substantially along each longitudinal side of said non-inflatable body area, said first and second other channels at each longitudinal side of said non-inflatable body area each having at least one row of apertures oriented towards said non-inflatable body area when the channels are inflated so that air output from the apertures is directed towards said non-inflatable body area.

12. Blanket of claim 9, wherein said plurality of apertures at each of said other channels along the longitudinal side of said non-inflatable body area comprise at least two in alignment sections of substantially evenly spaced apertures separated by a non-apertured section.

13. Blanket of claim 12, wherein said sections of apertures are arranged such that when said other channels are inflated, the apertures are oriented towards said non-inflatable body area so that air output from the apertures is directed towards said non-inflatable body area, no air being output from said non-apertu red section at each of said other channels.

14. Blanket of claim 9, wherein there are first and second other channels formed substantially along each longitudinal side of said non-inflatable body area, each of said first and second other channels at each longitudinal side of said non-inflatable body area having at least two in alignment sections of substantially evenly spaced apertures separated by a non-apertured section arranged along said each other channel such that the apertures are oriented towards said non-inflatable body area when said each other channel is inflated.

15. Blanket of claim 9, further comprising at least one fluid absorption pad positioned at at least one of said non-inflatable areas to absorb fluid collected thereat.

16. Blanket of claim 9, wherein there is one inlet provided at a junction at each side of the blanket where said head portion meets said body portion and a third inlet provided at the foot end of said blanket, each of the inlets adapted to be selectively opened to enable air to be input to said blanket.

17. Blanket of claim 1, wherein said plurality of apertures are formed as respective rows of apertures at least one of each being provided along a corresponding one of said other channels at the upper body portion of said blanket.

18. Blanket of claim 1, wherein said plurality of apertures are formed as respective rows of apertures at least one of each being provided along a corresponding one of said other channels at the lower body portion of said blanket.

19. Blanket of claim 9, wherein said plurality of apertures are formed at said one and other channels at the upper body portion of the blanket so that air output from said apertures is directed substantially toward the upper body portion of the patient lying on said blanket.

20. Blanket of claim 9, wherein said plurality of apertures are formed at said one and other channels at the lower body portion of the blanket so that air output from said apertures is directed substantially toward the lower body portion of the patient lying on said blanket.

* * * * *